United States Patent [19]

Evard et al.

[11] Patent Number: 5,425,705
[45] Date of Patent: Jun. 20, 1995

[54] THORACOSCOPIC DEVICES AND METHODS FOR ARRESTING THE HEART

[75] Inventors: Philip C. Evard, Palo Alto; Timothy R. Machold, Moss Beach; Hanson S. Gifford, III, Woodside; Alex T. Roth, Redwood City; Wesley D. Sterman, San Francisco; Lawrence C. Siegel, Hillsborough; Jeffry J. Grainger, Woodside, all of Calif.

[73] Assignee: Stanford Surgical Technologies, Inc., Redwood City, Calif.

[21] Appl. No.: 173,899

[22] Filed: Dec. 27, 1993

Related U.S. Application Data

[63] Continuation-in-part of Ser. No. 23,778, Feb. 22, 1993.
[51] Int. Cl.⁶ .............................................. A61M 25/01
[52] U.S. Cl. ...................................... 604/28; 604/53; 604/36; 604/92
[58] Field of Search ............................ 606/205–211; 604/19, 27–28, 36, 93, 115–117, 164; 51–53, 56, 44, 4

[56] References Cited

U.S. PATENT DOCUMENTS

| | | |
|---|---|---|
| 4,318,401 | 3/1982 | Zimmerman . |
| 4,531,935 | 7/1985 | Berryessa . |
| 4,531,936 | 7/1985 | Gordon . |
| 4,568,330 | 2/1986 | Kujawski et al. . |
| 4,610,661 | 9/1986 | Possis et al. . |
| 5,013,296 | 5/1991 | Buckberg et al. . |
| 5,167,628 | 12/1992 | Boyles . |
| 5,224,931 | 7/1993 | Kumar . |
| 5,330,498 | 7/1994 | Hill . |

OTHER PUBLICATIONS

Miltex M Surgical Instruments "Thoracic and Cardiovascular Instruments," Miltex Instrument Company, Inc. 1986 p. 319.
Pilling Surgical Instruments "Aortic Claims," 1993 pp. 348–351.

*Primary Examiner*—C. Fred Rosenbaum
*Assistant Examiner*—Perry E. Van Over
*Attorney, Agent, or Firm*—Townsend and Townsend Khourie and Crew

[57] ABSTRACT

The invention provides devices and methods for thoracoscopically arresting the heart and establishing cardiopulmonary bypass, thus facilitating a variety of less-invasive surgical procedures on and within the heart and great vessels of the thorax. In one embodiment, the invention provides a thoracoscopic system for arresting a patient's heart including a clamp configured for introduction into the patient's thoracic cavity through a percutaneous intercostal penetration in the patient's chest. The clamp is positionable about the patient's ascending aorta between the coronary arteries and the brachiocephalic artery. The clamp is coupled to the distal end of an elongated handle means for manipulating the clamp from a location outside of the patient's thoracic cavity. A means for actuating the clamp is coupled to the proximal end of the handle means. When actuated, the clamp blocks blood flow through the ascending aorta. A delivery cannula may be used to deliver cardioplegic fluid into the ascending aorta upstream from the clamp to arrest cardiac function.

20 Claims, 11 Drawing Sheets

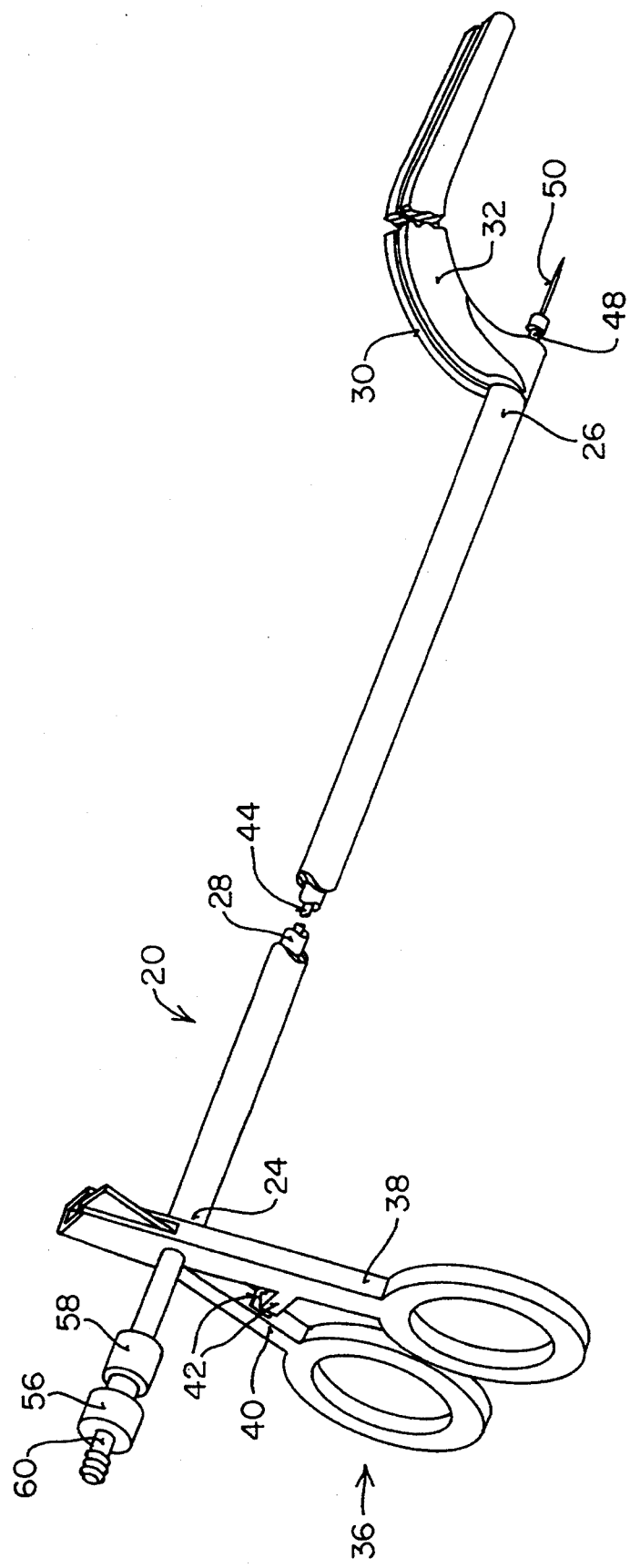
FIG_1

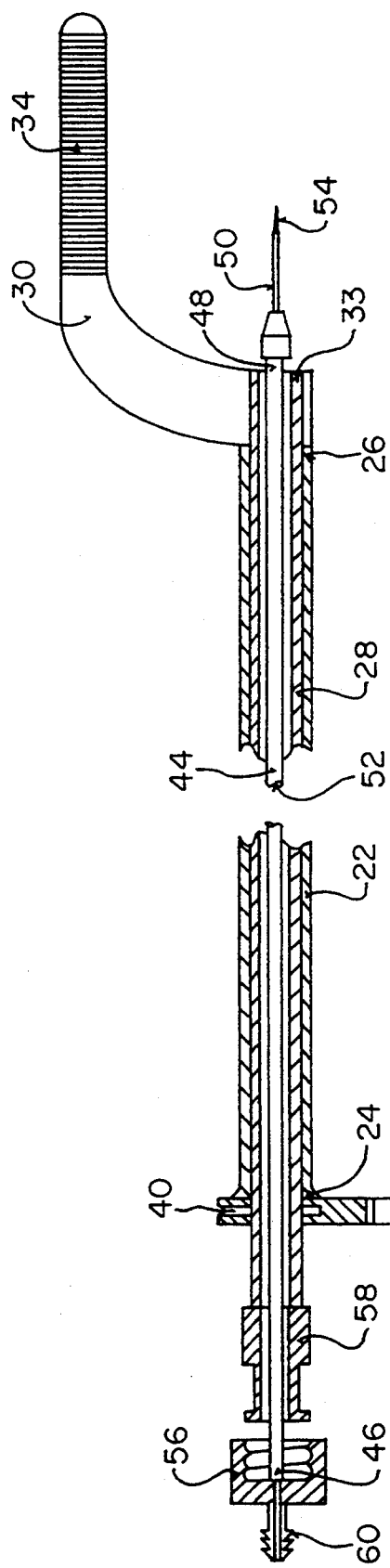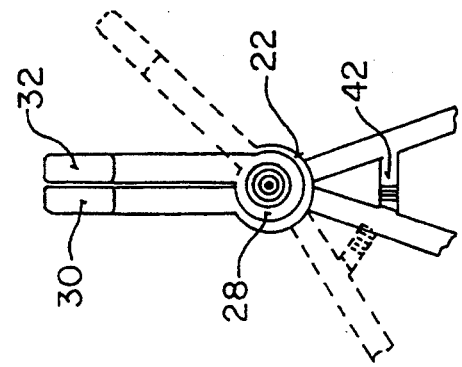
FIG_2A
FIG_2B

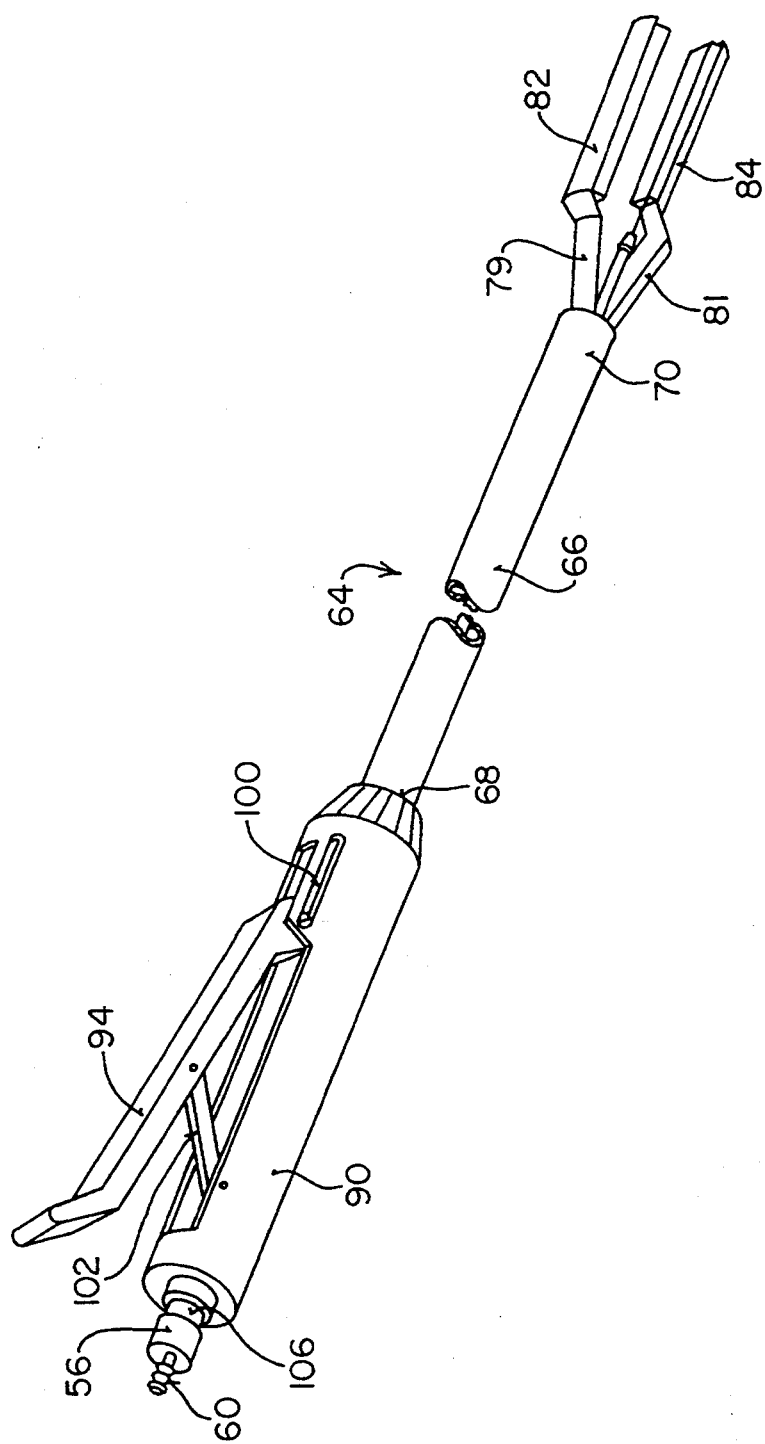

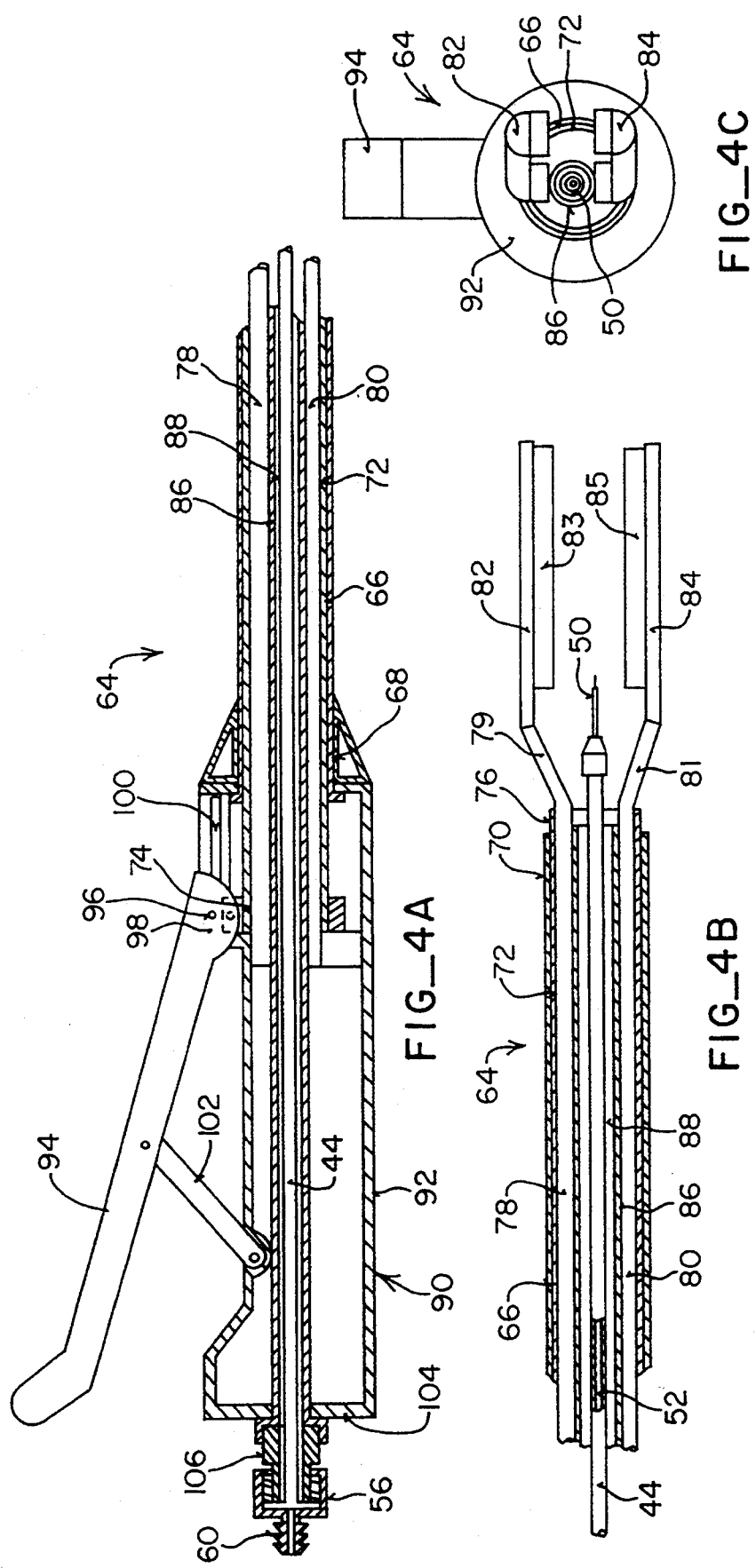

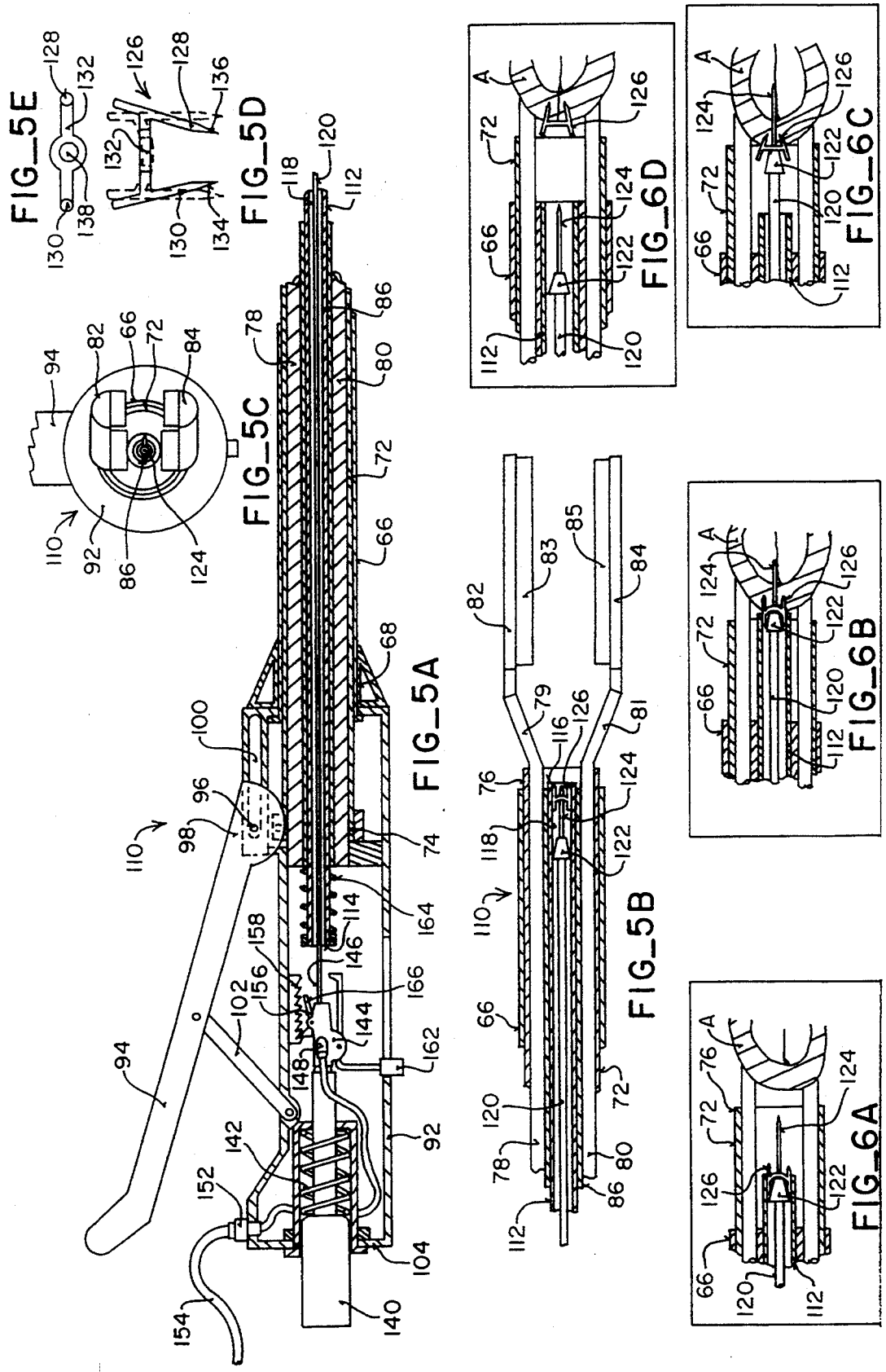

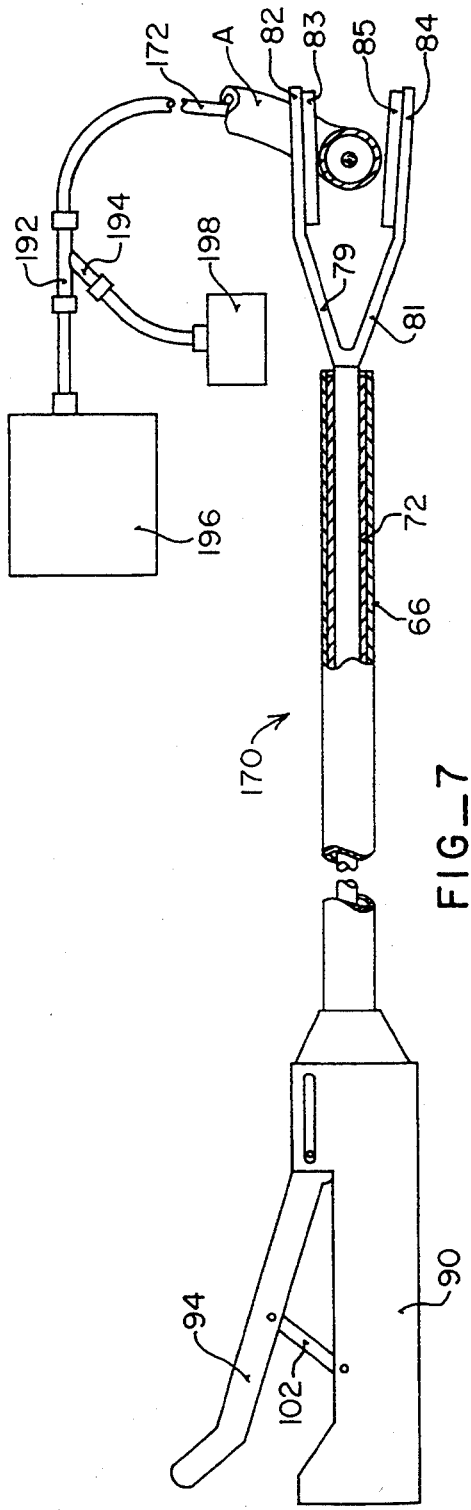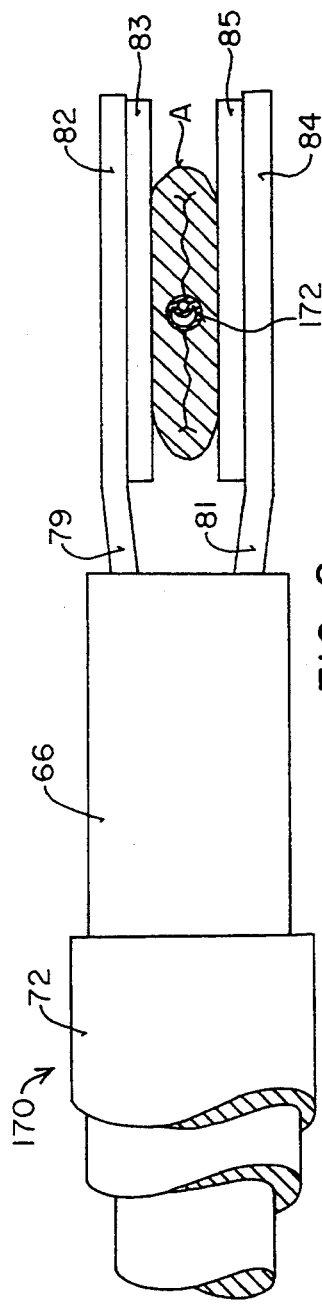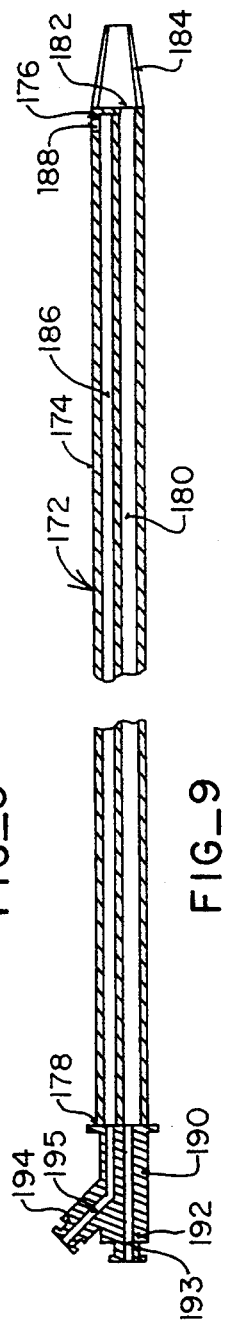

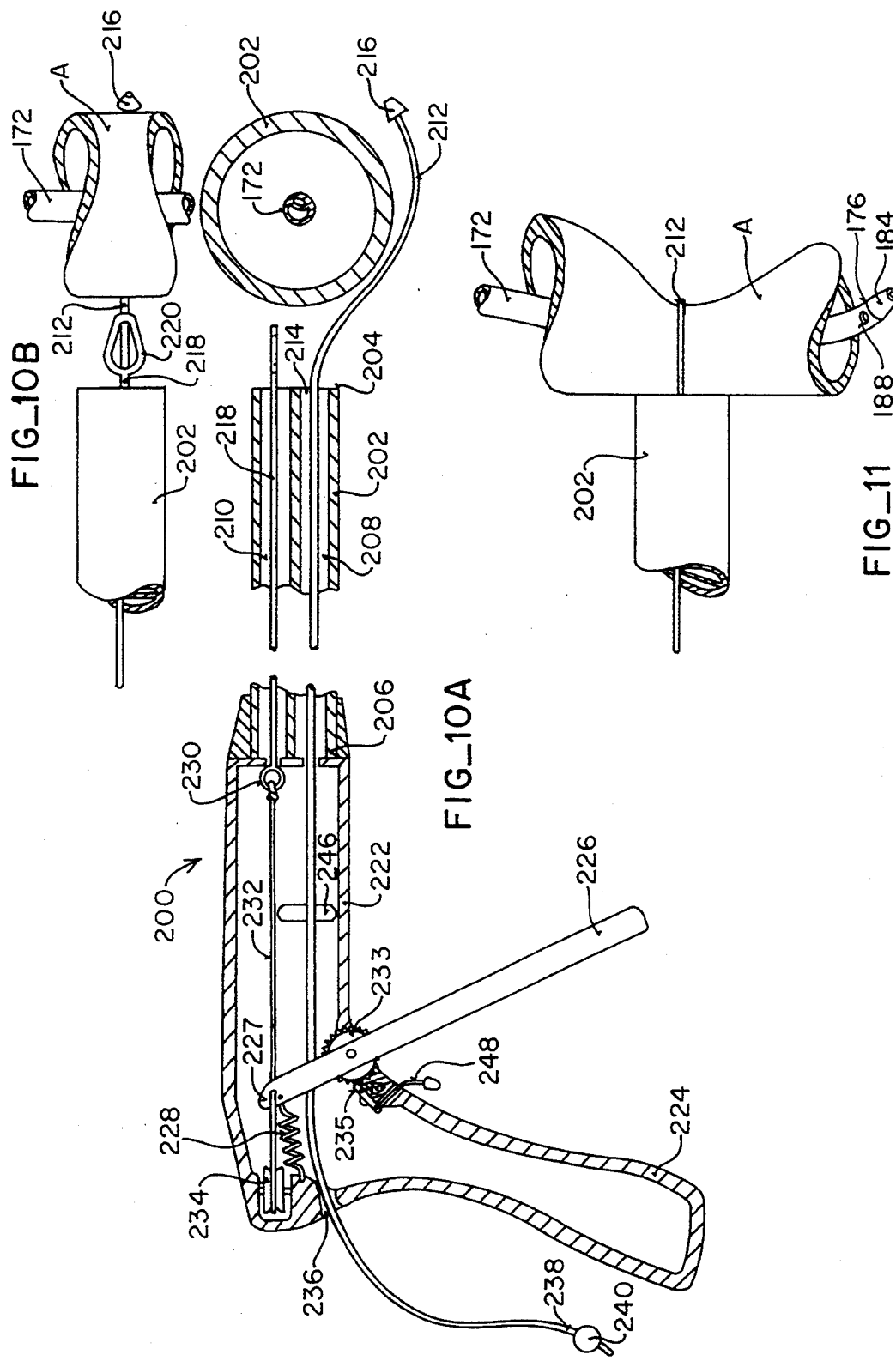

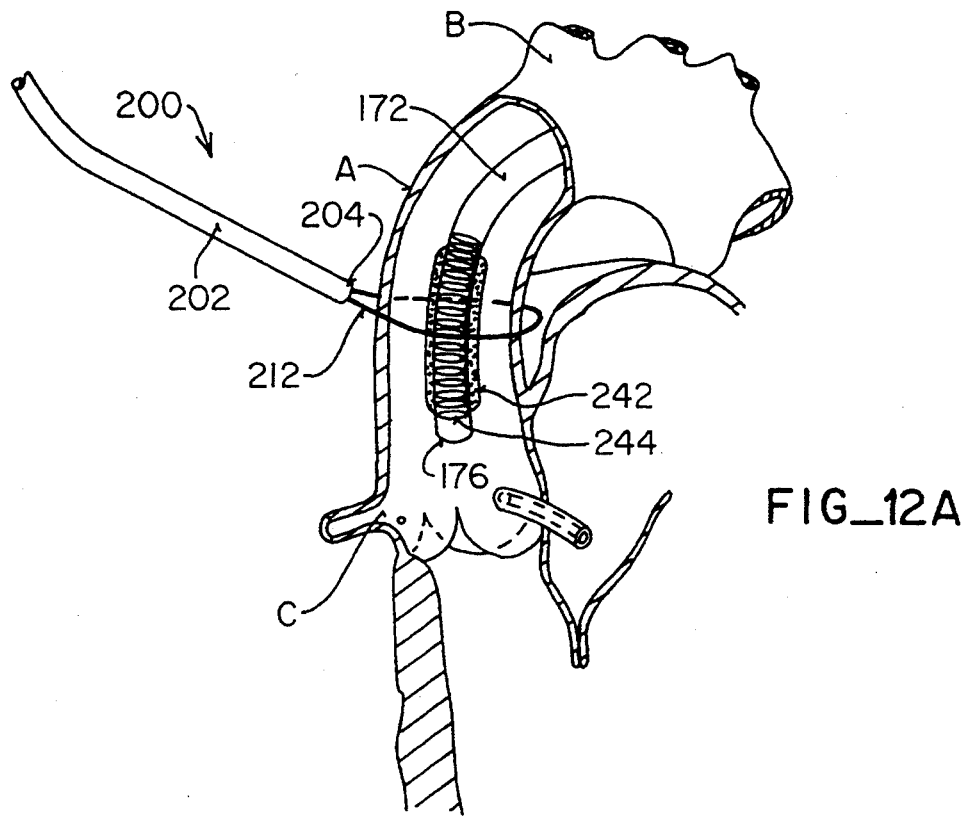
FIG_12A
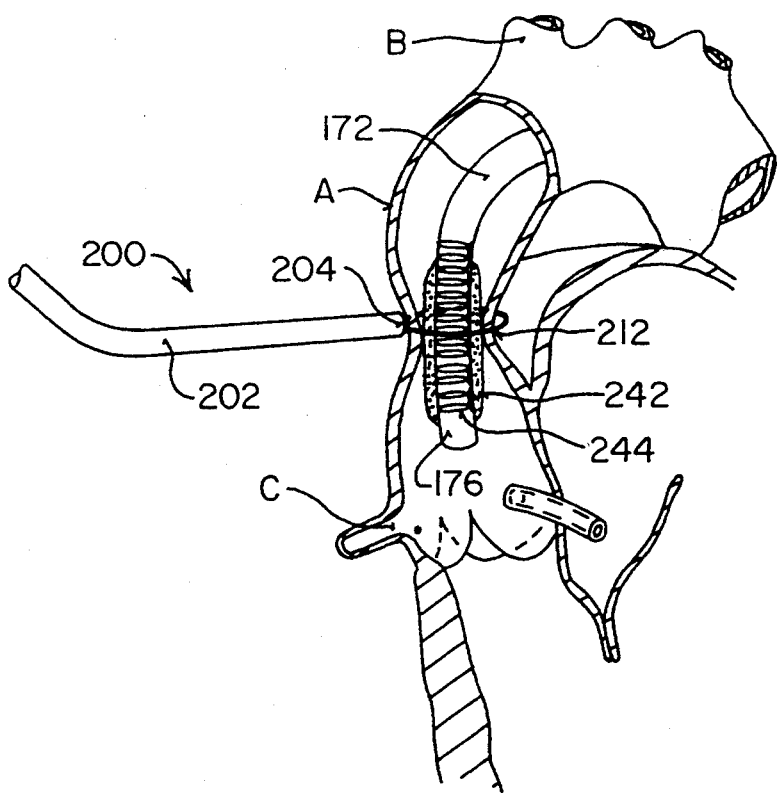
FIG_12B

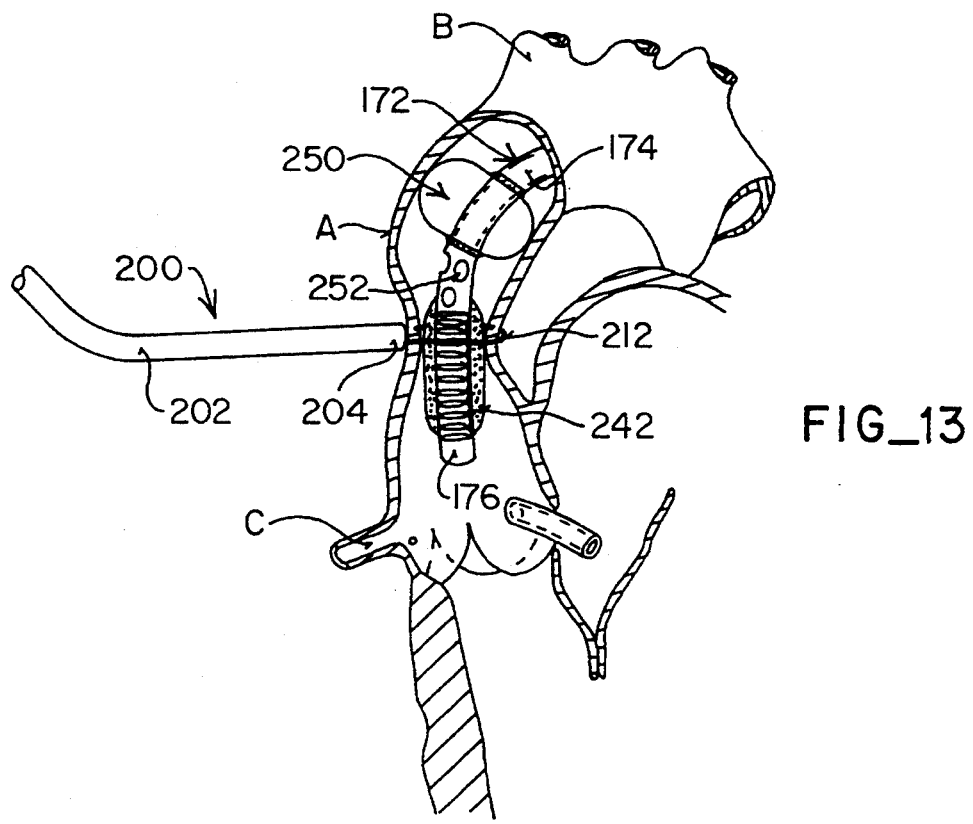
FIG_13
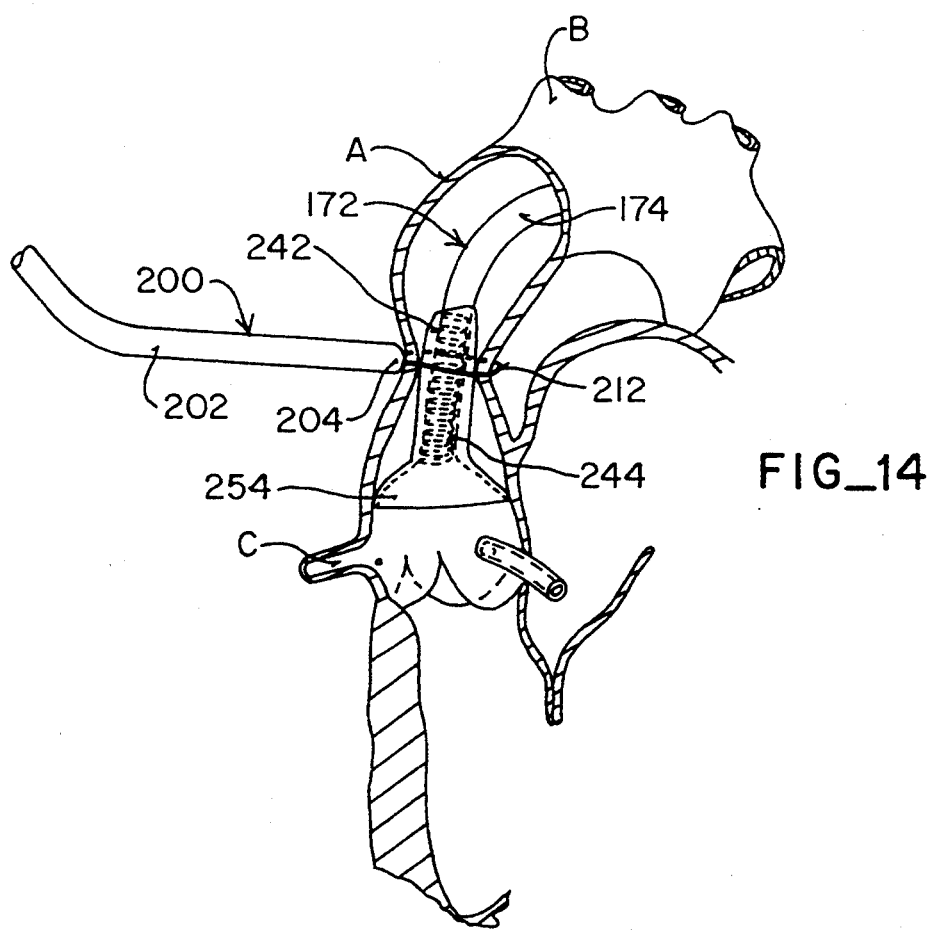
FIG_14

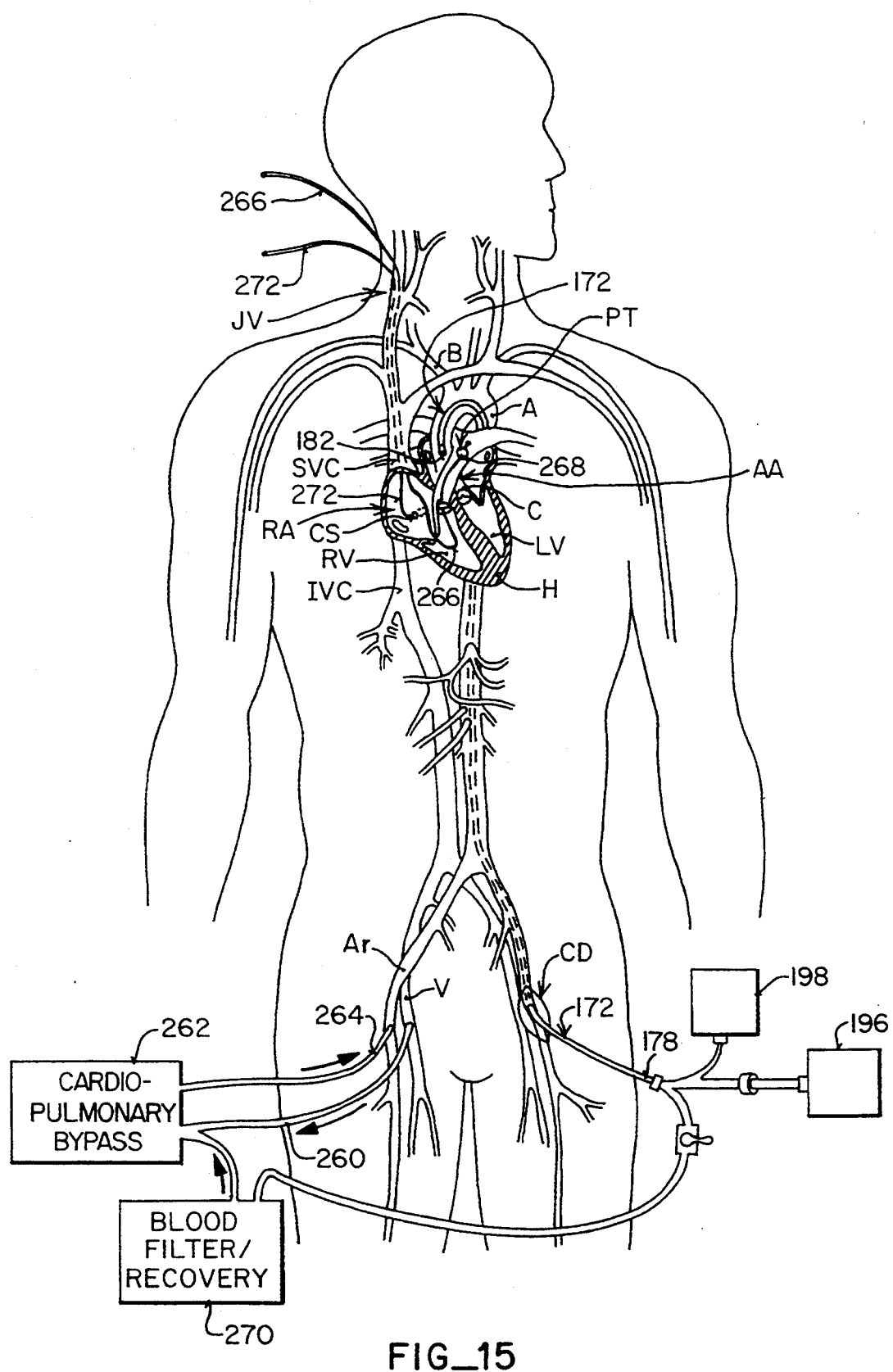
FIG_15

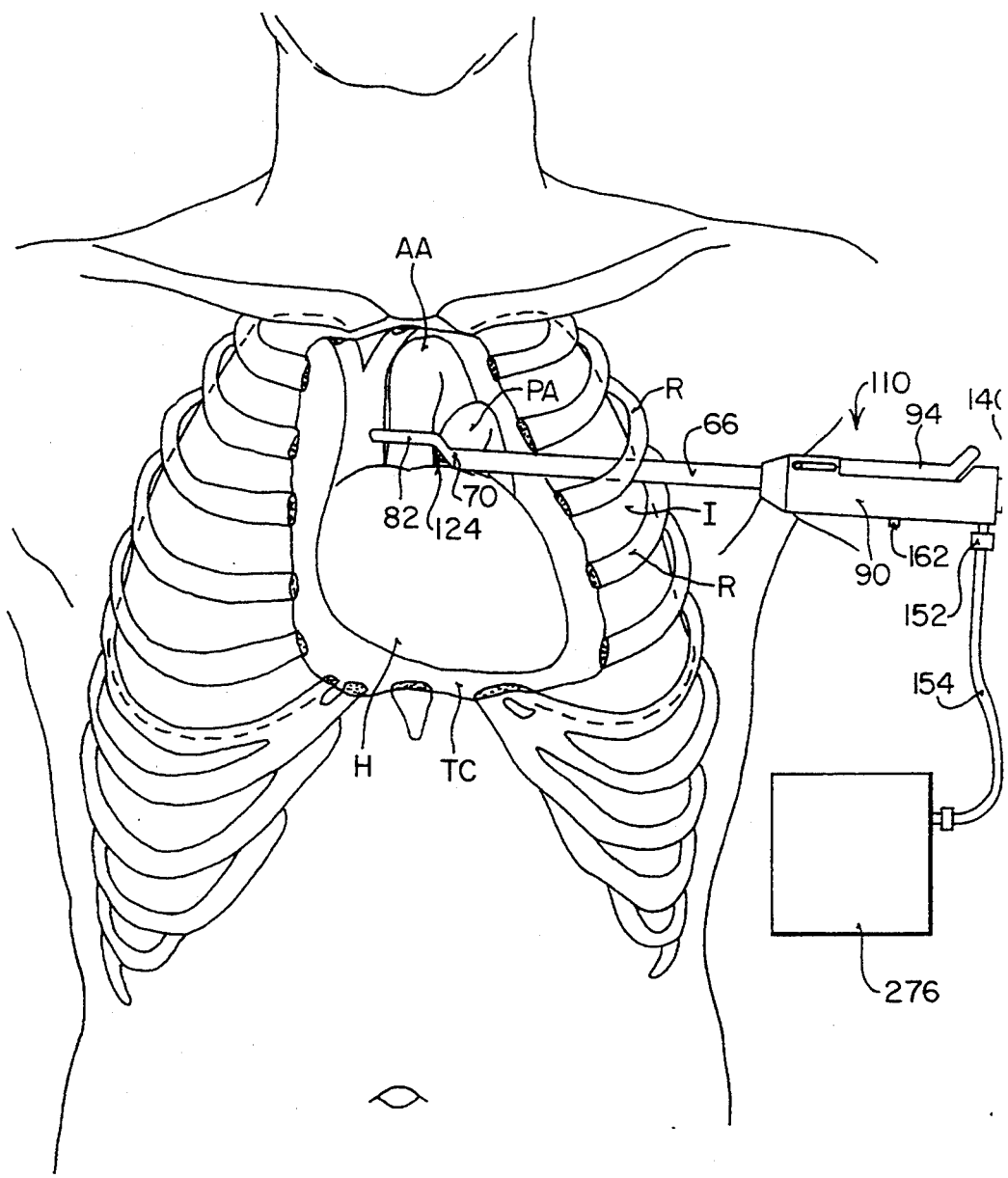
FIG_16

THORACOSCOPIC DEVICES AND METHODS FOR ARRESTING THE HEART

This application is a continuation-in-part of commonly-assigned, co-pending U.S. patent application Ser. No. 08/023,778, filed Feb. 22, 1993, the complete disclosure of which is hereby incorporated heroin by reference.

FIELD OF THE INVENTION

This invention relates generally to less-invasive surgical instruments for clamping, cannulation of, and infusion of fluids into hollow body structures. More specifically, the invention relates to less-invasive devices and methods for isolating the heart and coronary blood vessels from the remainder of the arterial system and delivering cardioplegic fluid to facilitate arresting cardiac function.

BACKGROUND OF THE INVENTION

Various cardiovascular, neurosurgical, pulmonary, and other interventional procedures, including repair or replacement of aortic, mitral, and other heart valves, repair of septal defects, pulmonary thrombectomy, coronary artery bypass grafting, angioplasty, atherectomy, treatment of aneurysms, electrophysiological mapping and ablation, and neurovascular procedures, may require general anesthesia, cardiopulmonary bypass, and arrest of cardiac function. In order to arrest cardiac function, the heart and coronary blood vessels must be isolated from the remainder of the circulatory system. This serves several purposes. First, such isolation facilitates infusion of cardioplegic fluid into the coronary arteries in order to perfuse the myocardium and thereby paralyze the heart, without allowing the cardioplegic fluid to be distributed elsewhere in the patient's circulatory system. Second, such isolation facilitates the use of a cardiopulmonary bypass system to maintain circulation of oxygenated blood throughout the circulatory system while the heart is stopped, without allowing such blood to reach the coronary arteries, which might resuscitate the heart. Third, in cardiac procedures, such isolation creates a working space into which the flow of blood and other fluids can be controlled or prevented so as to create an optimum surgical environment.

Circulatory isolation of the heart and coronary blood vessels is usually accomplished by placing a mechanical cross-clamp externally on the ascending aorta downstream of the ostia of the coronary arteries, but upstream of the brachiocephalic artery, so as to allow oxygenated blood from the cardiopulmonary bypass system to reach the arms, neck, head, and remainder of the body. Using conventional techniques, the sternum is cut longitudinally (a median sternotomy), providing access between opposing halves of the anterior portion of the rib cage to the heart and other thoracic vessels and organs. Alternatively, a lateral thoracotomy is formed, wherein a large incision is made between two ribs. A portion of one or more ribs may be permanently removed to optimize access. Through this large opening in the chest, a cross-clamp is placed externally on the ascending aorta, thereby isolating the heart and coronary arteries from the remainder of the arterial system. Frequently, the aorta must be dissected away from adjacent tissue to facilitate placement of such a cross-clamp.

To arrest cardiac function, a catheter is introduced through the sternotomy or thoracotomy and inserted through a puncture in the aortic wall into the ascending aorta between the cross-clamp and the aortic valve. Cardioplegic fluid is infused through the catheter into the aortic root and coronary arteries to perfuse the myocardium. An additional catheter may be introduced into the coronary sinus for retrograde perfusion of the myocardium with cardioplegic fluid. In addition, the myocardium is sometimes cooled by irrigation with cold saline solution and/or application of ice or cold packs to the outside of the heart. Cardiac contractions will then cease.

In surgical procedures requiring a median sternotomy or other form of gross thoracotomy, the ascending aorta is accessible by dissection for placement of an external cross-clamp through this large opening in the chest. However, such open-chest surgery often entails weeks of hospitalization and months of recuperation time, in addition to the pain mad trauma suffered by the patient. Moreover, the average mortality rate associated with this type of procedure is about two to fifteen per cent for first-time surgery, and mortality and morbidity are significantly increased for reoperation.

New devices and methods are therefore desired that facilitate the performance of cardiac procedures such as heart valve repair and replacement, coronary artery bypass grafting, and the like, using minimally invasive techniques, eliminating the need for a gross thoracotomy. Such techniques have been described in co-pending application Ser. No. 08/023,778, which is assigned to the assignee of the present invention and am incorporated heroin by reference. In that application methods and devices am described for performing coronary artery bypass grafting, and other procedures through small incisions or cannulae positioned in the chest wall, obviating the need for a gross thoracotomy. One technique described for attesting the heart during such procedures involves the use of a catheter which is introduced into a peripheral artery such as a femoral artery and positioned in the ascending aorta. An expandable member such as an inflatable balloon at the distal end of the catheter is expanded within the ascending aorta to block blood flow therethrough. Cardioplegic fluid may then be infused into the aortic root and into the coronary arteries through a lumen in the catheter, and/or in a retrograde manner through a catheter positioned in the coronary sinus, paralyzing the myocardium.

While this endovascular technique for arresting the heart provides significant advantages over conventional open-chest techniques, in some circumstances the use of an endovascular device for aortic partitioning may be undesirable. For example, in some cases the patient's femoral arteries and other vessels in which such a device could be introduced may not be suitable for such introduction, due to inadequate vessel diameter, vessel stenosis, vascular injury, or other conditions. In addition, where a number of endovascular cannulae are to be introduced to support cardiopulmonary bypass, retroperfusion of cardioplegic fluid, removal of blood from the heart, and other functions, a suitable arterial location for introduction of an endovascular aortic partitioning device may not be available. Further, it may be desirable to minimize the number of arterial punctures so as to reduce the risk of infection and other complications stemming from such punctures.

Methods and devices are therefore needed for isolating the heart and coronary arteries from the remainder of the arterial system and arresting cardiac function that eliminate the need for a gross thoracotomy, but do not rely upon endovascular access into the ascending aorta. The methods and devices should facilitate clamping the ascending aorta between the brachiocephalic artery and the coronary ostia so as to block blood flow therethrough, as well as delivering cardioplegic fluid into the ascending aorta upstream of the clamping location so as to perfuse the myocardium through the coronary arteries.

SUMMARY OF THE INVENTION

The invention provides less-invasive devices and methods for clamping and cannulating a hollow and/or tubular body structure and infusing a fluid therein. More specifically, the invention provides thoracoscopic methods and devices for isolating the heart and coronary blood vessels from the remainder of the arterial system and for delivering cardioplegic fluid to the myocardium so as to arrest cardiac function. The methods and devices of the invention eliminate the need for a median sternotomy or other form of gross thoracotomy to obtain access into the thoracic cavity. At the same time, the invention does not rely upon endovascular access into the ascending aorta through punctures in peripheral arteries, and is therefor useful when such punctures are undesirable, or where arterial access locations are unavailable due to inadequate vessel diameter, vessel stenosis, vascular injury, or other conditions.

In a preferred embodiment of the method of the invention, a clamp is introduced into the patient's thoracic cavity through a percutaneous intercostal penetration in the patient's chest. The clamp is positioned about the patient's aorta between the coronary arteries and the brachiocephalic artery. The clamp is actuated from outside of the patient's thoracic cavity so as to block blood flow through the aorta. A cardioplegic fluid delivery cannula is positioned within the aorta so that its distal end is upstream of the point blocked by the clamp. Cardioplegic fluid is then delivered into the aorta through a delivery lumen in the delivery cannula, thereby perfusing the myocardium through the coronary arteries so as to arrest the heart.

Because the patient's chest is preferably closed during the procedure except for one or more small percutaneous intercostal penetrations, visualization within the thoracic cavity is usually required to facilitate accurate positioning of the clamp and/or the delivery cannula. In an exemplary embodiment, a scope such as an endoscope or thoracoscope is positioned in a percutaneous intercostal penetration in the patient's chest to facilitate viewing at least a portion of the thoracic cavity. Alternatively, other methods of imaging may be used, such as ultrasound, transesophageal echocardiography, fluoroscopy, and the like.

In a first preferred embodiment, the delivery cannula is introduced into the aortic lumen by penetrating the aortic wall upstream of the clamp with the distal end of the delivery cannula. Preferably, the delivery cannula is coupled to the clamp by guiding means which guide the delivery cannula into the aorta at a predetermined location relative to the clamp.

In an alternative embodiment, the delivery cannula is introduced into a peripheral artery in the patient and transluminally positioned from the peripheral artery into the ascending aorta. Preferably, the delivery cannula is introduced into a femoral artery, and advanced toward the heart until the distal end is in the ascending aorta. The clamp is then actuated so as to seal the aortic lumen about the exterior of the delivery cannula.

The method may further include closing the penetration in the wall of the aorta after the cardioplegic fluid has been delivered. The step of closing may comprise applying a plug or patch to the penetration, suturing the penetration, or applying a staple to the aortic wall to close the penetration.

In a further aspect of the invention, a thoracoscopic system for arresting a patient's heart includes a clamp configured for introduction into the patient's thoracic cavity through a percutaneous intercostal penetration in the patient's chest. The clamp is positionable about the patient's ascending aorta between the coronary arteries and the brachiocephalic artery. The clamp is coupled to the distal end of an elongated handle means for manipulating the clamp from a location outside of the patient's thoracic cavity. A means for actuating the clamp is coupled to the proximal end of the handle means. When actuated, the clamp blocks blood flow through the ascending aorta.

The clamp may have various constructions. In a preferred embodiment, the clamp comprises a pair of jaws each having a contact surface for engaging opposing sides of the aorta. The jaws may be hinged, deflectable, rotatable, or otherwise movable from an open position suitable for positioning about the ascending aorta, to a clamping position configured to block blood flow through the aorta. The jaws may include atraumatic elements such as elastomeric pads or covers on the contact surfaces to reduce injury to the exterior of the aorta.

Alternatively, the clamp may have a noose-like configuration, comprising a flexible cable which may be wrapped around the aorta, and means for tensioning the cable. In this way, the aortic lumen may be constricted by tightening the cable until blood flow is blocked.

The system may further include means for delivering cardioplegic fluid into the aortic lumen upstream of the clamp from a location outside of the patient's thoracic cavity. In one embodiment, the means for delivering cardioplegic fluid comprises an endovascular delivery catheter transluminally positionable within the aortic lumen from an artery downstream of the ascending aorta, preferably a femoral artery. The clamp is configured to block blood flow through the aorta when the delivery catheter is positioned within the aortic lumen by sealing the aortic wall against the exterior surface of the delivery catheter. The delivery catheter has a port at its distal end in communication with an inner lumen extending within the catheter, through which cardioplegic fluid may be infused into the ascending aorta upstream of the clamp.

In an alternative embodiment, the means for delivering cardioplegic fluid comprises a delivery cannula positionable through a percutaneous penetration in the patient's chest. The distal end of the delivery cannula is configured to penetrate the aortic wall, and further includes a port in communication with a delivery lumen extending through the delivery cannula. A means for delivering cardioplegic fluid into the delivery lumen is provided at the proximal end of the cannula, allowing cardioplegic fluid to be infused into the ascending aorta upstream of the clamp.

The delivery, cannula is preferably coupled to the handle means and/or the clamp to facilitate penetration of the aorta at a predetermined location relative to the clamp. Usually, the delivery cannula is longitudinally slidable relative to the clamp. The handle means may be provided with an inner lumen through which the delivery cannula may be introduced into the thoracic cavity, or a guide means may be mounted to the exterior of the handle means so as to guide the delivery cannula as it enters the thoracic cavity and penetrates the aortic wall. Alternatively, the delivery cannula may be integrated into the handle means and may include an actuator mounted to the proximal end of the handle means, whereby the delivery cannula automatically penetrates the aortic wall when actuated. The delivery cannula may further be positionally adjustable relative to the clamp to allow selection of the location at which the cannula penetrates the aorta.

In an exemplary embodiment, the system includes means coupled to the distal end of the handle means/ or closing a penetration in the aorta formed by the delivery cannula. The closing means may have various configurations, but, in a preferred embodiment, comprises means for applying a staple to the wall of the aorta. Preferably, the staple is applied automatically as the delivery cannula is withdrawn from the aorta. The staple may be configured such that the ends of its legs are resiliently biased toward one another in an unstressed condition. The staple applying means may comprise a tubular sleeve coupled to the handle means and configured to hold a staple at its distal end with the legs of the staple spread apart so as to be generally parallel. The delivery cannula may be slidably disposed in the sleeve and configured to engage the staple as the delivery cannula is advanced distally. In this way, the staple may be driven into the aortic wall as the delivery cannula penetrates the aorta. When the delivery cannula is withdrawn, the staple remains in the aortic wall, the legs of the staple urging the penetration closed.

The delivery cannula may also be configured to penetrate the aorta in such a way as to require no closure means. For example, a plurality of very small needles may be used for penetrating the aorta, each needle forming a penetration small enough that little blood is lost from the aorta before a clot forms or the penetration closes.

A further understanding of the nature and advantages of the invention may be realized by reference to the remaining portions of the specification and the drawings.

BRIEF DESCRIPTION OF THE DRAWINGS

FIG. 1 is a perspective view of a first embodiment of a thoracoscopic aortic clamping device constructed in accordance with the principles of the present invention.

FIG. 2A is a side cross-sectional view of the aortic clamping device of FIG. 1.

FIG. 2B is a distal end view of the aortic clamping device of FIG. 1.

FIG. 3 is a perspective view of a second embodiment of a thoracoscopic aortic clamping device constructed in accordance with the principles of the present invention.

FIG. 4A is a side cross-sectional view of a proximal portion of the aortic clamping device of FIG. 3.

FIG. 4B is a side cross-sectional view of a distal portion or the aortic clamping device of FIG. 3.

FIG. 4C is a distal end view of the aortic clamping device of FIG. 3.

FIG. 5A is a side cross sectional view of a further embodiment of a thoracoscopic aortic clamping device constructed in accordance with the principles of the invention, showing a proximal portion thereof.

FIG. 5B is a side cross-sectional view or a distal portion of the aortic clamping device of FIG. 5A.

FIG. 5C is a distal end view of the aortic clamping device of FIG. 5A.

FIG. 5D is a front view of a staple for closing an aortic puncture in the aortic clamping device of FIG. 5A.

FIG. 5E is a top view of the staple of FIG. 5D.

FIGS. 6A–6D are side cross-sectional views of a distal portion of the aortic clamping device of FIG. 3 showing the delivery cannula penetrating the aortic wall and a means for closing the puncture in the aortic wall.

FIG. 7 is a side partial cross-sectional view of a further embodiment of a thoracoscopic aortic clamping device and delivery cannula constructed in accordance with the principles of the invention.

FIG. 8 is a side view of a distal portion of the aortic clamping device of FIG. 7.

FIG. 9 is a side cross-sectional view of the delivery cannula in the aortic clamping device of FIG. 7.

FIG. 10A is a side cross-sectional view of still another embodiment of an aortic clamping device and delivery cannula constructed in accordance with the principles of the invention.

FIG. 10B is a top view of a distal portion of the aortic clamping device of FIG. 10A in an unclamped configuration.

FIG. 11 is a top view of a distal portion of the aortic clamping device of FIG. 10A in a clamped configuration.

FIGS. 12A–12B are side views showing the aortic clamping device or FIG. 10A positioned in the patient's ascending aorta in an open configuration and a clamped configuration, respectively.

FIGS. 13 and 14 are side views illustrating alternative embodiments of the aortic clamping device of FIG. 10A positioned in the patient's ascending aorta.

FIG. 15 is a front view of a patient showing the positioning of the delivery cannula and cardiopulmonary bypass cannulae in the patient's circulatory system to facilitate arresting cardiac function.

FIG. 16 is a front view of the interior of a patient's thoracic cavity illustrating the positioning of the aortic clamping device of FIG. 3 about the patient's ascending aorta.

DETAILED DESCRIPTION OF SPECIFIC EMBODIMENTS

The devices and methods of the invention facilitate isolation of the heart and coronary blood vessels from the remainder of the arterial system using thoracoscopic techniques. In addition, the invention facilitates thoracoscopic and/or endovascular delivery of cardioplegic fluid to the myocardium so as to paralyze the heart. In this way, the invention allows cardiac function to be arrested and cardiopulmonary bypass to be established without the need for a median sternotomy or other form of gross thoracotomy, and without the need for the peripheral arterial access required by an endovascular aortic partitioning device. Once the patient is on cardiopulmonary bypass with the heart stopped, a variety of thoracoscopic, endovascular, or open surgical procedures may be performed, including coronary artery bypass grafting, heart valve repair and replacement, septal defect repair, pulmonary thrombectomy, removal of atrial myxoma, patent foramen ovale closure, treatment of aneurysms, myocardial drilling, electrophysiological mapping and ablation, angioplasty, atherectomy, connection of congenital defects, and other interventional procedures.

The terms "percutaneous intercostal penetration" and "intercostal penetration" as used herein refer to a penetration, in the form or a small cut, incision, hole, cannula, trocar sleeve, or the like through the chest wall between two adjacent ribs, wherein the patient's rib cage and sternum remain substantially intact, without cutting, removing, or significantly displacing the ribs or sternum. These terms are intended to distinguish a gross thoracotomy such as a median sternotomy, wherein the sternum and/or one or more ribs are cut or removed from the rib cage, or one or more ribs are retracted significantly, to create a large opening into the thoracic cavity. A "percutaneous intercostal penetration" may abut or overlap the adjacent ribs between which it is formed, but the maximum width of the penetration which is available for introduction of instruments into the thoracic cavity will be the width of the intercostal space, bounded by two adjacent ribs in their natural, substantially undeflected positions. It should be understood that one or more ribs may be retracted or deflected a small amount without departing from the scope of the invention; however, it is a specific objective of the invention to avoid the pain, trauma, and complications which result from the large incisions and/or significant deflection or cutting of the ribs in conventional, open-chest techniques.

A first preferred embodiment of a thoracoscopic aortic clamping device according to the invention is illustrated in FIGS. 1, 2A, and 2B. Device 20 includes a tubular outer shaft 22 having a proximal end 24 and a distal end 26. Outer shaft 22 preferably has a length of about 10 to 35 cm so that distal end 26 may reach the ascending aorta from a lateral side or an anterior side of the chest. A drive shaft 28 extends through outer shaft 22 and is axially rotatable therein. A fixed jaw 30 is mounted to distal end 26 of outer shaft 22. A movable jaw 32 is mounted to distal end 33 of drive shaft 28 in opposition to jaw 30 so as to facilitate clamping the aorta therebetween. Jaws 30, 32 each have a contact surface 34 configured to engage the exterior of the aorta, which may include textural features to enhance grip on the aorta. An elastomeric pad or cover (not shown) of silicone or other low durometer material may further be provided over contact surfaces 34 to reduce trauma on aortic tissue.

An actuator 36 is mounted at proximal end 24 of outer shaft 22. Actuator 36 includes a handle 38 mounted to proximal end 24 of outer shaft 22, and a movable handle 40 mounted to drive shaft 28. By pivoting handle 40 relative to handle 38, drive shaft 28 rotates within outer shaft 22, thereby opening and closing jaws 30, 32. A pair of notched extensions 42 on handles 38, 40 are configured to engage one another as the handles are closed, providing ratcheted locking of the device to maintain the jaws in a closed position.

Device 20 further includes a delivery cannula 44 for delivering cardioplegic fluid into the aorta while jaws 30, 32 are in a closed position on the aorta. Delivery cannula 44 has a proximal end 46 and a distal end 48 to which a needle 50 is attached. Needle 50 is dimensioned and configured to penetrate the ascending aortic wall into the aortic lumen, preferably having a length of about 1 cm to 3 cm. A delivery lumen 52 extends through cannula 44 and is in fluid communication with a port 54 near the distal end of needle 50. A luer fitting 56 is mounted to proximal end 46 of cannula 44, and is configured to engage a complementary luer fitting 58 mounted to the proximal end of drive shaft 28. Luer fitting 56 includes a barb 60 for connecting a hose (not shown) for delivering cardioplegic fluid into delivery lumen 52. Usually, the hose will be connected to a cardioplegic fluid pump designed to deliver a continual or periodic flow of cardioplegic fluid into the aorta during a procedure.

It may be seen that jaws 30, 32 are offset from the central longitudinal axis of outer shaft 22 and drive shaft 28 so as to permit introduction of needle 50 into the aorta upstream from the point at which jaws 30, 32 clamp the aorta.

Needle 50 is usually in the range of 10 gauge to 16 gauge so as to facilitate infusion of cardioplegic fluid into the aorta at a ram sufficient to paralyze the myocardium and to maintain such paralysis. Preferably, the size of needle 50 is minimized so that the puncture made in the ascending aorta will not bleed excessively when needle 50 is withdrawn from the aortic wall. However, in some cases, the puncture will require closure by means of sutures, staples, or other means, as described more fully below. To avoid the need for such closure, a plurality of smaller needles may be mounted to distal end 48 of delivery cannula 44 as an alternative to a single larger needle 50. The number and size of the needles are selected to provide an adequate total flow rate of cardioplegic fluid into the aorta, yet each needle is sufficiently small, e.g. less than about 0.025 in. outer diameter, so that each puncture need not be closed after withdrawal of the needles from the aortic wall due to normal blood clotting.

A second preferred embodiment of a thoracoscopic aortic clamping device according to the invention is illustrated in FIGS. 3 and 4A–4C. In this embodiment, device 64 includes a tubular outer shaft 66 having a proximal end 68 and a distal end 70. A tubular inner shaft 72 is slidably disposed within outer shaft 66 and has a proximal end 74 and a distal end 76. A pair of jaw extensions 78, 80 are disposed within inner shaft 72, each having an outwardly angled distal portion 79, 81 to which is attached one of offset jaws 82, 84. A core tube 86 is disposed between jaw extensions 78, 80 within inner shaft 72, and an inner lumen 88 extends through core tube 86. Delivery cannula 44 (described above) may be inserted through inner lumen 88 so that needle 50 extends distally from the distal end 76 of inner shaft 72. As best illustrated in FIG. 4C, jaws 82, 84 are offset from the central longitudinal axis of outer shaft 70 and inner shaft 76 so as to permit introduction of needle 50 into the aorta upstream from the point at which jaws 82, 84 clamp the aorta. Jaws 82, 84 may have a pair of elastomeric pads 83, 85 of silicone or other low durometer material to reduce trauma when clamped on the aorta.

A handle 90 is attached to the proximal end 68 of outer shaft 66 and includes a housing 92 to which is coupled a lever 94. A pin 96 extends through a distal end 98 of lever 94, and is slidable within a pair of slots 100 in housing 92. A link 102 is pivotally coupled at one end to lever 94 in a middle portion thereof, and at the other end to housing 92 proximal to slots 100. Inner shaft 72 is attached at its proximal end 74 to distal end 98 of lever 94. In this way, pivoting lever 94 toward housing 92 translates the lever distally within slots 100, thus translating inner shall 72 distally over jaw extensions 78, 80. Distal end 76 of inner shaft 72 engages angled distal portions 79, 81 of jaw extensions 78, 80, thus urging jaws 82, 84 toward each other. A spring (not shown) may be mounted between housing 92 and lever 94 to bias lever 94 against housing 92 to maintain jaws 82, 84 in a closed or clamped position.

Core tube 86 is fixed to housing 92 at a proximal end 104 thereof. A luer fitting 106 is mounted to the exterior of housing 92 and has an interior passage in communication with inner lumen 88. When jaws 82, 84 have been clamped onto the patient's aorta, delivery cannula 44 may be inserted through inner lumen 88 until needle 50 penetrates the aortic wall upstream of jaws 82, 84. Luer fitting 56 on delivery cannula 44 may be locked onto luer fitting 106 on housing 92. A hose may be connected to barb 60 on delivery cannula 44 to deliver cardioplegic fluid into the aorta through delivery lumen 52.

As described above, the aortic puncture created by needle 50 may sometimes require closure after withdrawal of the needle to prevent excessive bleeding when cardiac function is restored. Such closure may be performed by means of thoracoscopic instruments, such as staple appliers or suturing instruments. Alternatively, a means for closing the aortic puncture may be integrated into the aortic clamping device of the invention. An example of such a device is illustrated in FIGS 5A–5D and 6A–6D. In this embodiment, clamping device 110 comprises the same jaw configuration, handle, and jaw closure mechanism as the embodiment of FIGS. 3 and 4A–4B. Device 110 further includes an inner sleeve 112 slidably disposed within core tube 86 and having a proximal end 114, a distal end 116 and a lumen 118 therebetween. A delivery tube 120 resides within lumen 118 and has a fitting 122 at its distal end to which a needle 124 is attached.

Distal end 116 of inner sleeve 112 is configured to retain a staple 126 within lumen 118. Staple 126 comprises, as shown in FIGS. 5D–5E, at least two legs 128, 130 connected by a flexible cross member 132. Legs 128, 130 have distal points 134, 136 for penetrating aortic wall tissue. In an unstressed condition, legs 128, 130 are disposed at an angle between about 60° and 87° relative to cross member 132 such that points 134, 136 are closer together than the remainder of legs 128, 130. Legs 128, 130 may be deflected outward so as to be parallel to each other, whereby cross member 132 is deflected into a curved configuration, (shown in phantom in FIG. 5D). When legs 128, 130 are released, cross-member 132 resiliently returns to its unstressed shape, returning legs 128, 130 to their angled disposition. In this way, staple 126 may be applied to the aorta with legs 128, 130 parallel, and, when released, legs 128, 130 crimp the aortic tissue therebetween without requiring a separate crimping or closure means. In alternative configurations, staple 126 may have three, four, or more legs with inwardly disposed distal points. Shallow axial channels (not shown) may be provided on opposing sides of lumen 118 extending proximally from distal end 116 in which legs 128, 130 may be retained to maintain axial alignment of staple 126.

As shown in FIG. 5E, cross member 132 has a bore 138 in a middle portion thereof that is larger than needle 124, but smaller than fitting 122. The staple is held within lumen 118 so that needle 124 is aligned with bore 138. As shown in FIGS. 6A–6B, by distally advancing sleeve 112 and delivery tube 120 in tandem, needle 124 penetrates the aortic wall while staple 126 is applied to aorta A with legs 128, 130 parallel. Sleeve 112 may then be retracted proximally while delivery tube 120 remains in position, wherein fitting 122 holds staple 126 in the aortic wall and legs 128, 130 return to their unstressed, angled configuration (FIG. 6C). When cardioplegic fluid delivery is complete, delivery robe 120 may be retracted, removing needle 124 from aorta A and leaving staple 126 in the aortic wall to close the puncture created by needle 124 (FIG. 6D).

The means for actuating sleeve 112 and delivery tube 120 will be described with reference to FIG. 5A. An actuation button 140 is mounted at the proximal end of housing 92 and is biased in an outward position by a spring 142. Actuation button 140 is coupled to an adaptor 144 fixed to proximal end 146 of delivery tube 120. Adaptor 144 has an inner chamber (not shown) in communication with the interior of delivery tube 120. An arm 148 on adaptor 144 has an inner passage (not shown) in communication with the inner chamber of adaptor 144 and is configured for connection to a flexible tube 150. Tube 150 connects to a fitting 152 mounted to housing 92, which may be connected to a hose 154 from a cardioplegic fluid delivery device.

A pawl 156 is pivotally mounted to adaptor 144 and is biased by a spring (not shown) to engage a set of linear teeth 158 on housing 92, thus providing a ratcheted locking mechanism to maintain actuator button 140 in a depressed position. A catch 160 is pivotally mounted to adaptor 144 and is biased in a counterclockwise direction. As actuator button 140 is depressed, delivery robe 120 advances distally relative to sleeve 112 until catch 160 engages proximal end 114 of sleeve 112, at which point needle 124 and staple 126 are in the position shown in FIG. 6A. Further depression of actuator button 140 advances delivery tube 120 and sleeve 112 in tandem, allowing needle 124 and staple 126 to penetrate the aortic wall, as shown in FIG. 6B. Delivery of cardioplegic fluid into aorta A may then be initiated through hose 154, tube 150, delivery tube 120, and needle 124. When the procedure is complete, cardioplegic fluid delivery is terminated and a release button 162 is pressed, which pivots catch 160 in a clockwise direction, allowing sleeve 112 to retract proximally under the force of a spring 164 disposed about the proximal end of sleeve 112. At this point, sleeve 112, delivery tube 120, and staple 126 are in the positions shown in FIG. 6C. Sleeve 112 retracts relative to delivery tube 120 until its proximal end 114 engages a release arm 166 on pawl 156, disengaging pawl 156 from teeth 158 and allowing delivery cannula 120 and actuator button 140 to retract. In this way, with the press of a single release button, needle 124 is removed from aorta A and staple 126 is applied to aortic wall to close the puncture created by needle 124, as illustrated in FIG. 6D. Staple 126 may remain in the patient's body indefinitely, may be resorbable, or may be surgically removed using thoracoscopic instruments after clotting has occurred or the aortic puncture has healed.

A further embodiment of an aortic clamping device according to the invention is illustrated in FIGS. 7–9. In this embodiment, clamping device 170 is constructed in large part like the embodiment of FIGS. 3 and 4A–4C, except that no inner lumen 88 is required for insertion of a delivery cannula 44, and that jaws 82, 84 need not be offset from the central axis of shafts 66, 72 to allow the delivery cannula to penetrate the aorta upstream from the point at which the aorta is clamped. In the present embodiment, the need to penetrate the aorta is obviated by the use of an endovascular delivery cannula 172 positioned within the aortic lumen between jaws 82, 84.

As shown in FIG. 9, delivery cannula 172 comprises a flexible shaft 174 of a biocompatible polymer such as polyurethane, polyvinyl chloride, polyether block amide, or polyethylene, with a distal end 176, a proximal end 178, and at least one inner lumen 180 therebetween. A port 182 is disposed at distal end 176 in fluid communication with inner lumen 180, to facilitate infusion of cardioplegic fluid into the aorta. A soft tip 184 may be provided on distal end 176 to reduce the risk of injury to vessel walls, to the aortic valve, or to other tissue. A second lumen 186 may also be provided with a port 188 near distal end 176, to facilitate infusion or aspiration of fluids, pressure measurement, and the like. An adaptor 190 is attached to proximal end 178 and has a first arm 192 with a passage 193 in communication with inner lumen 180 and a second arm 194 with a passage 195 in communication with second lumen 186. First arm 192 may be connected to a hose from a cardioplegic fluid delivery pump, while second arm 194 may be connected to a pressure measurement device, aspiration device, fluid delivery device, or the like.

As illustrated in FIGS. 7–8, delivery cannula 172 is positioned in the aorta A, with distal end 176 in the ascending aorta between the brachiocephalic artery and the coronary ostia. Shaft 174 preferably has a length of at least about 80 cm to allow introduction into a femoral artery and transluminal positioning of distal end 176 in the ascending aorta. First arm 192 may be connected to a cardioplegic fluid supply 196, while second arm 194 may be connected to a pressure measurement device 198. Jaws 82, 84 of aortic clamping device 170 are positioned about the ascending aorta A between the brachiocephalic artery and the coronary arteries. Jaws 82, 84 are then closed on aorta A by actuating lever 94, which extends inner shaft 66 over angled segments 79, 81. Jaws 82, 84 are closed until the opposing sides of aorta A engage one another and seal about the exterior of delivery cannula 172, as shown in FIG. 8. Cardioplegic fluid may then be delivered through inner lumen 180, while the pressure within the aorta upstream of clamping device 170 may be measured through second lumen 186.

Referring now to FIGS 10A–10B and 11, a further embodiment of an aortic clamping device according to the invention will be described. In this embodiment, aortic clamping device 200 comprises a shaft 202 having a distal end 204, a proximal end 206, and first and second lumens 208, 210 extending therebetween. A flexible cable or strap 212 is slidably disposed in first lumen 208 and extends distally through an opening 214 in distal end 204. An anchor 216 is attached to the distal end of cable 212. A wire 218 is slidably disposed in second lumen 210 and has a loop 220 extending distally from distal end 204 of shaft 202. Loop 220 has a width which narrows in the distal direction, so that anchor 216 may be passed through a proximal portion of loop 222, and trapped in a distal portion of loop 220.

A handle 222 is attached to proximal end 204 of shaft 202 and has a grip 224 suitable for grasping with the user's hand. A lever 226 is pivotally mounted to handle 222 and has an upper end 227 to which a spring 228 is attached to bias upper end 227 in a proximal direction. Wire 218 has a second loop 230 at its proximal end to which is attached a flexible cord 232. Cord 232 extends around a pulley 234 rotatably coupled to handle 222 and attaches to upper end 227 of lever 226. A gear 233 is mounted to lever 226 and is engaged by a pawl 235 pivotally mounted to handle 222. Cable 212 extends through handle 222 and exits through an opening 236, with a proximal end 238 disposed outside of handle 222. An anchor ball 240 is attached to proximal end 238 and has a width larger than that of opening 236 to prevent passage therethrough. Anchor ball 240 may be configured to allow adjustment of its longitudinal position on cable 212 to facilitate use of device 200 on aortas of various sizes.

Usually, aortic clamping device 200 is used in conjunction with delivery cannula 172, described above in connection with FIGS. 7–9. As shown in FIGS. 12A–12B, delivery cannula 172 is first introduced into the patient's arterial system, usually through a femoral artery, and advanced so that distal end 176 is in the ascending aorta A between brachiocephalic artery B and coronary ostia C. Aortic clamping device 200 is positioned so that distal end 204 is adjacent the aorta at the point it is to be clamped. As shown in FIGS. 10A–10B, cable 212 is wrapped around aorta A, usually by means of conventional thoracoscopic instruments such as forceps and/or needle drivers, and anchor 216 is inserted through loop 220. Lever 226 is then actuated, drawing anchor 216 and cable 212 proximally through lumen 210 so as to tighten cable 212 around aorta A until the aortic wall seals against the exterior of delivery cannula 172, as shown in FIGS. 11 and 12B.

In an exemplary embodiment, as shown in FIGS. 12A–12B, delivery cannula 172 has a pad 242 of silicone or other low durometer polymer fixed to its exterior near distal end 176 to minimize trauma to the aortic wall and to resist movement of the cannula during clamping. A stiffener coil 244 embedded in shaft 174 may also be provided to maintain the patency of lumens 180, 186 during clamping. In addition, shaft 202 may be bendable to facilitate positioning shaft 202 through an intercostal space with distal end 204 near the ascending aorta.

To release aortic clamping device 200 from aorta A, cable 212 may be severed by inserting a scissors or knife through side port 246 in handle 222, thereby releasing tension on cable 212 and allowing the device 200 to be withdrawn from the thoracic cavity. Alternatively, anchor ball 240 may be configured to be removable from proximal end 238 of cable 212. Or, a release cord 248 coupled to pawl 235 may be provided to facilitate disengaging pawl 235 from gear 233, allowing lever 226 to return to its outward position, thereby releasing tension on cable 212. Anchor 216 may then be removed from loop 220 using thoracoscopic instruments, allowing device 200 to be removed from the thoracic cavity.

FIGS. 13 and 14 illustrate two alternative constructions of delivery cannula 172 in conjunction with aortic clamping device 200. In the embodiment of FIG. 13, delivery cannula 172 includes a balloon 250 attached to shaft 174 and spaced proximally from distal end 176 a sufficient distance to allow aorta A to be clamped about shaft 174 distal to balloon 250. The interior of balloon 250 is in communication with an inflation lumen (not shown) in shalt 174 for delivery of an inflation fluid into the balloon, and is configured to fully occlude the aortic lumen when inflated. A plurality of ports 252 are provided in shaft 174 distal to balloon 250 and are in communication with an aspiration lumen (not shown) within shaft 274. In this way, when cable 212 is released after a procedure, any air, fluids, thrombus, and/or other emboli which might have been produced are prevented from flowing downstream by balloon 250, and may be aspirated from the arterial system through ports 252.

In the embodiment of FIG. 14, delivery cannula 172 includes an aortic occlusion means 254 at distal end 176 of shaft 174. Occlusion means 254 is configured to completely occlude the aortic lumen, and may be funnel-shaped with a tapered interior passage in communication with an aspiration lumen (not shown) in shaft 174. In this way, air, fluids, thrombus, and/or other emboli which might be produced during a procedure distal to the point of clamping are trapped in occlusion means 254 and may be withdrawn from the arterial system through the aspiration lumen in delivery catheter 174. Occlusion means 254 is preferably a soft collapsible material to allow it to be collapsed and inserted into a sheath for introduction. The sheath may be positioned in the ascending aorta, then retracted to allow occlusion means 254 to expand and occlude aorta A. Aortic clamping device 200 may then be used to clamp aorta A about shaft 174.

The method of the invention will now be described with reference to FIGS. 15 and 16. The patient is first placed on cardiopulmonary bypass, using the system illustrated in FIG. 15. A venous cannula 260 is positioned in a vein V of the patient, preferably a femoral vein in the groin area, and advanced into the inferior vena cava IVC and/or into the interior of heart H to withdraw deoxygenated blood therefrom. Venous cannula 260 may alternatively be introduced thoracoscopically into the inferior vena cava IVC, into the superior vena cava SVC, or into the right atrium RA. Venous cannula 260 is connected to a cardiopulmonary bypass system 262 which receives the withdrawn blood, oxygenates the blood, and returns the oxygenated blood to an arterial return cannula 264 positioned in an artery Ar, preferably a femoral artery. Arterial return cannula 264 may alternatively be introduced thoracoscopically directly into a descending portion of the aorta A.

A pulmonary venting catheter 266 may also be utilized to withdraw blood from the pulmonary trunk PT. Pulmonary venting catheter 266 may be introduced from the neck through the internal jugular vein JV and superior vena cava SVC, or from the groin through femoral vein V and interior vena cava IVC. Usually, a Swan-Ganz catheter (not shown) is first introduced and positioned in pulmonary trunk PT using well-known techniques, and pulmonary venting catheter 266 is then introduced over the Swan-Ganz catheter. Blood is withdrawn from pulmonary trunk PT through a port at the distal end of pulmonary venting catheter 266 and an inner lumen extending through the catheter outside of the patient's body. Pulmonary venting catheter 266 may further have one or more balloons 268 at its distal end proximal to the distal port for occluding pulmonary trunk PT.

An alternative method of venting blood from pulmonary trunk PT is described in U.S. Pat. No. 4,889,137, which is incorporated herein by reference. In the technique described therein, a catheter is positioned from the internal jugular vein JV in the neck through the fight atrium, right ventricle, and pulmonary valve into the pulmonary trunk PT. The catheter has a coil about its periphery which holds the pulmonary valve open so as to drain blood from pulmonary trunk PT, thereby decompressing the left side of the heart.

For purposes of arresting cardiac function, a delivery cannula 172 may be positioned in a femoral artery Ar by a percutaneous technique such as the Seldinger technique, or through a surgical cut-down CD. Delivery cannula 172 is advanced, usually over a guidewire (not shown), until its distal end 176 is disposed in the ascending aorta AA between the coronary ostia C and the brachiocephalic artery B. Blood may be vented from ascending aorta AA through a port 182 at the distal end of delivery cannula 172 in communication with inner lumen 180 in delivery cannula 172, through which blood may flow to proximal end 178. The blood may then be directed to a blood filter/recovery system 270 to remove emboli, and then returned to the patient's arterial system via CPB system 262.

Ascending aorta AA may then be clamped using one of the various embodiments of aortic clamping device described above. FIG. 16 illustrates the use of aortic clamping device 110 of FIGS. 5A–5D. Shaft 66 or clamping device 110 is positioned through the chest wall and into the thoracic cavity TC through an intercostal space I between two adjacent ribs R. A trocar sleeve may be positioned in the chest wall within an intercostal space to facilitate introduction of clamping device 110. An endoscope positioned in thoracic cavity TC through and intercostal space I may be used for visualization to facilitate accurate positioning of clamping device 110. Jaws 82, 84 are positioned on opposing sides of ascending aorta AA between brachiocephalic artery B and coronary ostia C (FIG. 15). Lever 94 is then actuated to close jaws 82, 84 on ascending aorta AA, stopping blood flow therethrough.

When it is desired to arrest cardiac function, a cardioplegic fluid such as potassium chloride (KCl) is delivered to the myocardium in at least one of several ways. Clamping device 110 includes an integrated cardioplegic fluid delivery cannula 120 (FIGS. 5A–5D), which may be activated by depressing actuator button. 140 on handle 90. Needle 124 will penetrate the aortic wall upstream of jaws 82, 84, and cardioplegic fluid may be delivered into the ascending aorta by means of a cardioplegic fluid pump 276 connected to fitting 152 in communication with delivery cannula 120.

As alternative or addition to delivery by means of clamping device 110, cardioplegic fluid may be delivered in an anterograde manner from a cardioplegic fluid pump 196 through inner lumen 180 in delivery cannula 172 into the ascending aorta upstream of the point at which the aorta is clamped. The cardioplegic fluid flows from the ascending aorta AA into the coronary arteries and paralyzes the myocardium. It should be noted that, when using clamping device 110 with integrated delivery cannula 120, endovascular delivery cannula 172 need not be utilized. However, it may be desirable to utilize such a cannula to facilitate pressure measurement, aspiration of air, fluids, thrombus, and other emboli from the aortic lumen, as well as supplementary delivery of cardioplegic fluid.

In addition, cardioplegic fluid may be delivered in a retrograde manner through a retroperfusion catheter 272 positioned in the coronary sinus CS. Retroperfusion catheter 272 may be positioned, usually over a guidewire (not shown), from the neck through the internal jugular vein JV and superior vena cava SVC, or from the groin through a femoral vein V and the inferior vena cava IVC. Retroperfusion catheter 272 may have one or more balloons (not shown) at its distal end to enhance positioning and infusion of cardioplegia into the coronary sinus. Cardioplegic fluid may thus be infused through the coronary veins into the capillary beds, paralyzing the myocardium.

Following delivery of cardioplegic fluid into the aortic lumen, cardiac function will quickly cease. The patient is now prepared for an interventional procedure to be performed. A variety of thoracoscopic, endovascular, or open surgical procedures may be performed, including coronary artery bypass grafting, heart valve repair and replacement, septal defect repair, pulmonary thrombectomy, removal of atrial myxoma, patent foramen ovale closure, treatment of aneurysms, myocardial drilling, electrophysiological mapping and ablation, angioplasty, atherectomy, correction of congenital defects, and other interventional procedures. Less-invasive techniques for performing such procedures are described in commonly-assigned copending applications Ser. No. 08/023,778, and Ser. No. 08/ (Attorney Docket No. 14635-3-1/SST No. 93005-1, filed Dec. 6, 1993), which have been incorporated herein by reference.

When it is desired to restore cardiac function, infusion of cardioplegic fluid through thoracoscopic delivery cannula 120, endovascular delivery cannula 172 and/or retroperfusion catheter 272 is discontinued. Blood, other fluids, air, thrombus, and other emboli within the heart or coronary arteries may then be aspirated through inner lumen 180 of delivery cannula 172, as well as through venous cannula 260 and/or pulmonary venting catheter 266. Release button 162 on clamping device 110 may then be depressed, causing needle 124 to retract from aorta A and leaving a staple 126 (FIGS. 6A–6D) in the aortic wall to close the puncture created therein. If the clamping device utilized does not include a means for closing the aortic puncture, conventional thoracoscopic instruments may be used to suture or staple the aortic puncture closed, if necessary.

Lever 94 on clamping device 110 may then be released, opening jaws 82, 84 to allow warm, oxygenated blood to flow into the coronary arteries to perfuse the myocardium. Cardiac contractions will usually begin soon thereafter. In some cases, electrical defibrillation may be necessary to help restore cardiac function. Clamping device 110 is withdrawn from the thoracic cavity. Any trocar sleeves used in the procedure are then removed, and thoracoscopic incisions are sutured or stapled closed. Delivery catheter 172 and retroperfusion catheter 272 may be removed from the patient. Cardiopulmonary bypass is then discontinued, and arterial cannula 264, venous cannula 260, and pulmonary venting catheter 266 are removed from the patient. Vascular punctures are closed.

While the clamping device of the invention has been described specifically with reference to aortic clamping for purposes of arresting the heart, it will be understood to those of skill in the art that the invention is useful in a variety of other interventional procedures as well. For example, the clamping device of the invention may be used for clamping, cannulation of, and fluid infusion into blood vessels other than the aorta, as well as structures such as the bowel, bile duct, colon, and various other tubular ducts and organs.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A method of arresting a heart in a thoracic cavity of a patient, the method comprising:
   viewing an interior portion of the patient's thoracic cavity through a scope positioned in a percutaneous intercostal penetration in the patient's chest;
   introducing a clamp into the patient's thoracic cavity through a percutaneous intercostal penetration in the patient's chest;
   positioning the clamp about an aorta between a coronary artery and a brachiocephalic artery, under visualization by means of the scope, the aorta having an aortic lumen through which blood flows from the heart;
   actuating the clamp from a location outside of the patient's thoracic cavity so as to block blood flow through the aortic lumen; and
   delivering cardioplegic fluid into the aortic lumen upstream of the clamp through a delivery lumen of a delivery cannula, the delivery cannula having a distal end disposed within the aortic lumen upstream of the clamp, and a proximal end disposed outside of the thoracic cavity.

2. The method of claim 1 wherein the delivery cannula extends through a percutaneous penetration in the patient's chest.

3. The method of claim 2 wherein the delivery cannula is introduced into the aortic lumen by penetrating a wall of the aorta with a distal end of the delivery cannula.

4. The method of claim 3 further comprising guiding the delivery cannula so as to penetrate the wall of the aorta at a predetermined location relative to the clamp.

5. The method of claim 4 wherein the delivery cannula is guided by guide means coupled to the clamp.

6. The method of claim 1 wherein the delivery cannula is introduced into a peripheral artery in the patient and transluminally positioned into the aortic lumen of the ascending aorta.

7. The method of claim 6 wherein the delivery cannula is introduced into a femoral artery.

8. The method of claim 6 wherein the delivery cannula is positioned in the ascending aorta before the clamp is actuated to block the aortic lumen.

9. The method of claim 1 wherein the clamp is fixed to a distal end of an elongated shaft positionable through an intercostal penetration in the patient's chest.

10. The method of claim 9 wherein the clamp is actuated by means of an actuator coupled to the proximal end of the shaft.

11. The method of claim 3 further comprising, after delivering the cardioplegic fluid, closing the penetration in the wall of the aorta.

12. The method of claim 11 wherein the step of closing comprises applying a plug or patch to the penetration.

13. The method of claim 11 wherein the step of closing comprises suturing the penetration closed.

14. The method of claim 11 wherein the step of closing comprises applying a staple to the aortic wall.

15. The method of claim 11 wherein a means for closing the penetration is mounted to a device selected from the group including the clamp and the delivery cannula, the closing means being actuated from outside the thoracic cavity.

16. A method of infusing fluid into an aorta in a body cavity of a patient, a the method comprising:
   introducing a clamp into the body cavity through a percutaneous penetration;
   positioning the clamp about the aorta, the aorta having an inner lumen;
   actuating the clamp from a location outside of the patient's body cavity so as to block the inner lumen of the aorta; and delivering the fluid into the inner lumen of the aorta through a delivery lumen of a delivery cannula extending through a percutaneous penetration into this body cavity the delivery cannula having a distal end disposed within the inner lumen, and a proximal end disposed outside of the body cavity.

17. The method of claim 16 wherein the fluid comprises cardioplegic fluid.

18. The method of claim 16 wherein the clamp is positioned about the aorta between a coronary artery and a brachiocephalic artery.

19. The method of claim 16 wherein the delivery cannula is coupled to the clamp.

20. The method of claim 16 wherein the delivery cannula is transluminally positioned from a peripheral artery into the inner lumen of the aorta.

* * * * *